United States Patent
Mistler

(10) Patent No.: US 7,673,632 B1
(45) Date of Patent: Mar. 9, 2010

(54) CONDOM

(76) Inventor: William Thomas Mistler, 3514 Lancaster Ave., #216, Philadelphia, PA (US) 19104

( * ) Notice: Subject to any disclaimer, the term of this patent is extended or adjusted under 35 U.S.C. 154(b) by 113 days.

(21) Appl. No.: 11/983,022

(22) Filed: Nov. 6, 2007

(51) Int. Cl.
*A61F 6/04* (2006.01)
*A61F 6/02* (2006.01)
*A61F 5/44* (2006.01)

(52) U.S. Cl. ............... 128/844; 128/842; 128/918; 604/349

(58) Field of Classification Search .......... 128/842, 128/844, 918; 604/349; 206/69
See application file for complete search history.

(56) References Cited

U.S. PATENT DOCUMENTS

| | | | | |
|---|---|---|---|---|
| 2,567,926 | A | * | 9/1951 | Dunkelberger .......... 128/844 |
| 2,670,736 | A | * | 3/1954 | Dunkelberger .......... 128/844 |
| 4,840,188 | A | | 6/1989 | Heidenfelder |
| 4,920,983 | A | | 5/1990 | Jimenez et al. |
| 5,018,532 | A | | 5/1991 | Etheredge, III |
| 5,163,448 | A | | 11/1992 | Foldesy |
| 5,411,034 | A | | 5/1995 | Beck et al. |
| 5,454,379 | A | * | 10/1995 | Shepherd .......... 128/842 |
| 5,666,972 | A | * | 9/1997 | Gifford .......... 128/842 |
| 5,758,659 | A | | 6/1998 | Thompson |
| 5,829,440 | A | * | 11/1998 | Broad, Jr. .......... 128/842 |
| 5,965,276 | A | | 10/1999 | Shlenker et al. |
| 6,135,112 | A | | 10/2000 | Harrison et al. |
| 6,308,708 | B2 | * | 10/2001 | Strauss et al. .......... 128/842 |
| 6,367,477 | B2 | | 4/2002 | Lee |
| D484,235 | S | | 12/2003 | Strenk et al. |
| 6,732,736 | B2 | | 5/2004 | Sanchez |
| 6,895,968 | B2 | * | 5/2005 | Shapiro et al. .......... 128/844 |
| 6,929,118 | B1 | | 8/2005 | Izz |
| 7,121,281 | B2 | | 10/2006 | Tsugawa |
| 2007/0181134 | A1 | * | 8/2007 | Lang .......... 128/844 |
| 2009/0090368 | A1 | * | 4/2009 | Attila .......... 128/844 |

FOREIGN PATENT DOCUMENTS

| | | |
|---|---|---|
| CN | 1099996 | 3/1995 |
| FR | 2750318 | 1/1998 |
| JP | 7100160 | 4/1995 |
| JP | 8089524 | 4/1996 |

OTHER PUBLICATIONS http://flipeasy.mazdaq.com/splash.asp, Flipeasy.com, Jul. 9, 2008, website screen shot.

* cited by examiner

*Primary Examiner*—Patricia Bianco
*Assistant Examiner*—Victoria Hicks
(74) *Attorney, Agent, or Firm*—Eckert Seamans Cherin & Mellott, LLC; David C. Jenkins, Esq.

(57) ABSTRACT

A condom having an indicia disposed on the lower side of the roll when the condom is in the rolled configuration. Preferably, the indicia is a fluorescent marking disposed on the inner side of the condom disposed at a location so that, when the condom is in the rolled configuration, the indicia is visible from the lower side only. More preferably, the indicia is a ring-shaped marking extending about the inner side of the tubular body. In this configuration, a user holding a rolled condom can easily determine which is the upper side of the roll and which is the lower side of the roll. The user may then quickly orient the condom with the lower side facing toward the penis and unroll the condom in the proper direction.

20 Claims, 2 Drawing Sheets

CONDOM

BACKGROUND OF THE INVENTION

1. Field of the Invention

This invention relates to a condom and, more specifically, to a condom having an indicia indicating the proper orientation for use.

2. Background Information

Condoms are well known prophylactic devices. The condom is typically made from latex or another plastic, however, natural condoms are still in use. A condom includes a thin, elastic, generally tubular body having an open first end, an elongated medial section, and a closed second end section thereby defining a partially enclosed space. Further, the body, as well as each of the elements set forth in the prior sentence, has an inner side and an outer side. Typically, the open end includes an elastic ring or rib. When used, the penis is disposed in the partially enclosed space with the inner side of the condom contacting the penis.

While condoms are used in an unrolled, or unfurled, configuration, condoms are typically stored in a rolled configuration. The rolled configuration is created by rolling the rib over the outer side of the body medial section. That is, in the rolled configuration, the condom includes a ring-like roll having multiple layers of the medial section of the body being wound about the first end rib. As the rib is initially rolled over the outer side of the body medial section, the outer side of the body medial section is disposed immediately adjacent to the rib. Thus, the exposed side of the roll is the inner side of the body medial section. With each revolution of the roll, the inner side of the body medial section is placed into contact with the exposed section of the roll while the corresponding inner side of the body medial section, i.e. the outer side of the body medial section directly opposite the inner side of the body medial section that is being placed into contact with the exposed section, becomes the outer side of the roll.

In this configuration, the second, closed end of the condom is not part of the roll and extends across the opening in the roll. The roll may be said to have an upper side and a lower side. The roll upper side includes the outer side of the second, closed end while the lower side includes the inner side of the second, closed end. As noted above, the roll always has a section of the inner side of the body medial section exposed. Thus, to wear the condom correctly, the user must unroll the condom with the lower side, and therefore the inner side of the second closed end and medial section, contacting the penis.

Users often have difficulty orienting the condom properly with the lower side of the roll facing downwardly. That is, the upper and lower sides of a rolled condom have a nearly identical appearance. Thus, users who are often distracted by the associated physical activity and/or may be in a dim or dark area, may attempt to put on the condom with the upper side, and therefore the outer surface of the condom, against the penis. Due to the direction of the roll, the condom cannot be unrolled when it is put on upside down.

While the mis-orientation of the condom is easily corrected, many users find such fumbling with a prophylactic device to interrupt what is, hopefully, a passionate activity. As such, many users choose to forego use of a condom and thereby potentially expose themselves, and their partners, to various diseases and the possibility of pregnancy.

SUMMARY OF THE INVENTION

The present invention discloses a condom having an indicia disposed on the lower side of the roll when the condom is in the rolled configuration. Preferably, the indicia is a fluorescent marking disposed on the inner side of the condom disposed at a location so that, when the condom is in the rolled configuration, the indicia is visible from the lower side only. More preferably, the indicia is a ring-shaped marking extending about the inner side of the tubular body. In this configuration, a user holding the condom can easily determine which is the upper side of the roll and which is the lower side of the roll. The user may then quickly orient the condom with the lower side facing toward the penis and unroll the condom in the proper direction.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

As used herein, the "user" is the male wearing the condom and, as described, is the person handling the condom. It is understood that a condom may be handled by someone other than the person wearing the condom.

As used herein, "fluorescent" shall mean any very bright and/or dazzling color and does not require the color and/or substrate to fluoresce.

Figure 1:
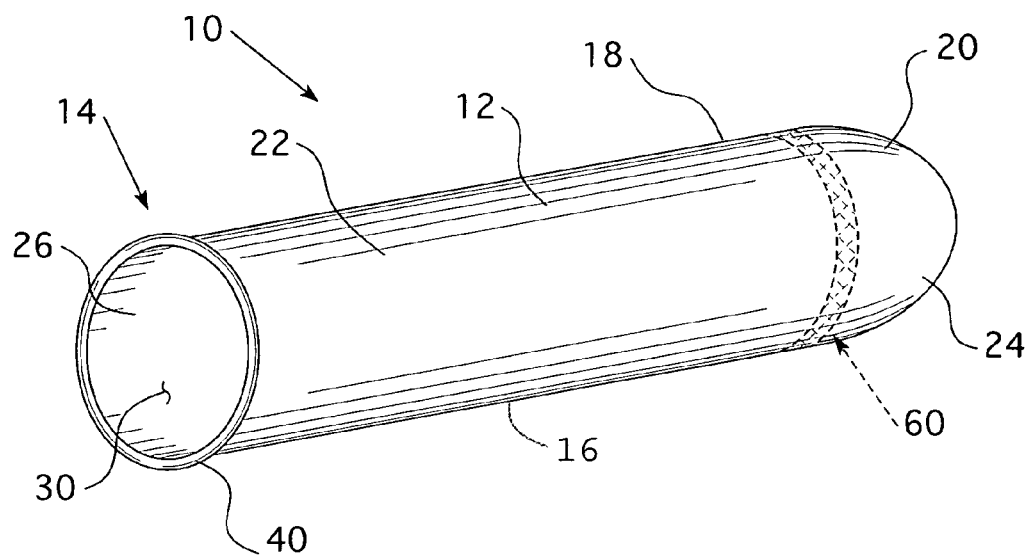
FIG. 1 is an isometric view of a condom.
Figure 4:
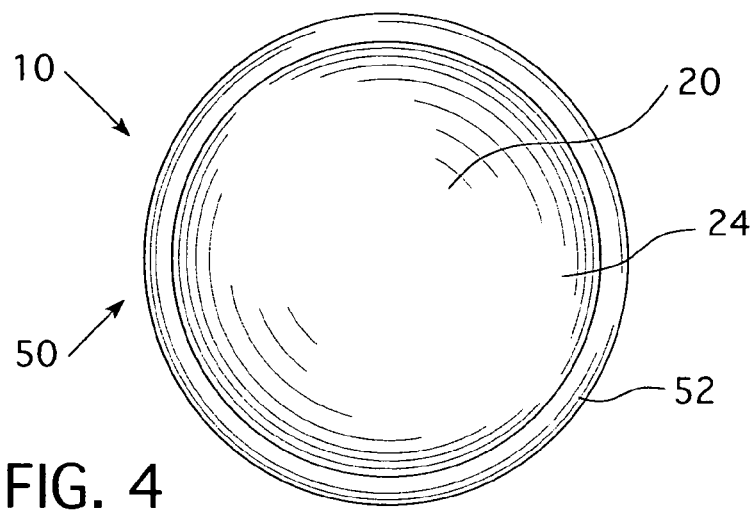
FIG. 4 is a top view of a rolled condom.
Figure 5:
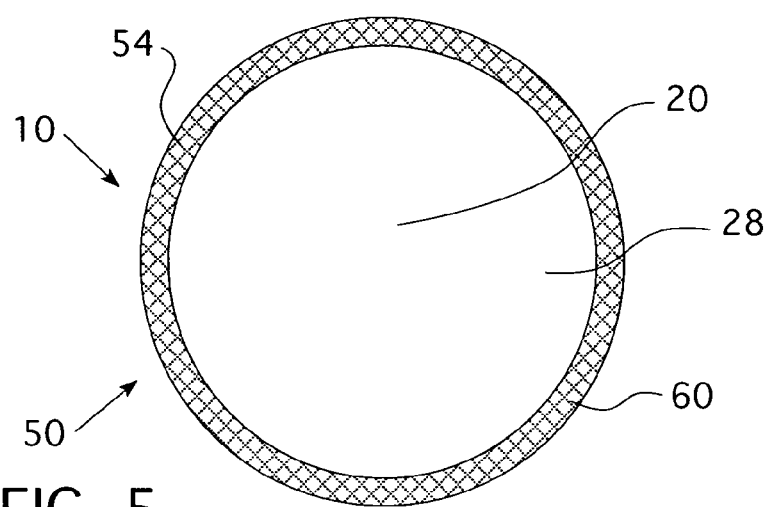
FIG. 5 is a bottom view of a rolled condom.

As shown in FIG. 1, a condom 10 is shown in a second, unrolled configuration. As described below, and as shown in FIGS. 4 and 5, the condom 10 is typically stored in a first, rolled configuration. The condom 10, which is typically made from a thin, elastic latex or plastic, has a generally circular tubular body 12 having an open first end 14, an elongated medial section 16, a second end 18 and a closed second end section 20. The closed second end section 20 is coupled to, and preferably formed as an integral part of, the body second end 18. The closed second end section 20, preferably, is shaped as a convex dome. The body 12 and the closed second end section 20 each have an outer side 22, 24 and an inner side 26, 28 (FIG. 5), respectively. Preferably, the body outer side 22 and the second end section outer side 24 form a contiguous surface. Similarly, the body inner side 26 and the second end section inner side 28 preferably form a contiguous surface. Thus, the body 12 and the closed second end section 20 define a generally enclosed space 30. The body first end 14 preferably includes a reinforced rib 40. The rib 40 is shaped as a generally circular torus and is made from the same material as the body 12. Typically, the rib 40 is formed as an integral part of the body first end 14.

Figure 2:
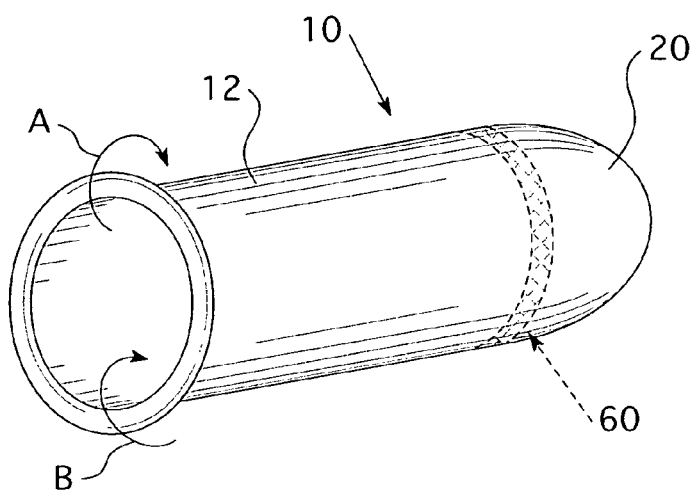
FIG. 2 is an isometric view of a partially rolled condom.
Figure 3:
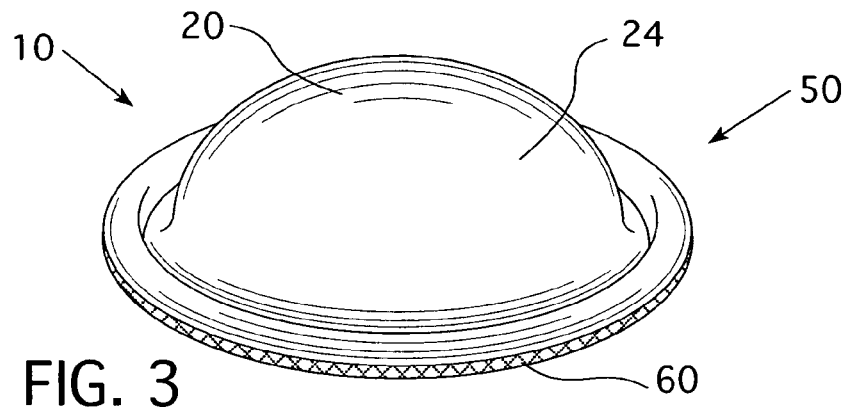
FIG. 3 is an isometric view of a rolled condom.

The condom 10, as noted above, is typically stored in a first, rolled configuration. Thus, after the condom 10 is formed, typically on an elongated mandrill, the condom 10 is rolled as shown in FIG. 2 as indicated by the arrow "A." That is, the body first end 14 and/or the rib 40 is rolled over the body outer side 22. The body first end 14, and/or the rib 40, is rolled over substantially all of the body medial section 16. The process of rolling the condom 10 creates a roll 50, as shown in FIGS. 3-5, that is a generally circular torus having multiple layers of the body medial section 16 wound about the body first end 14 and/or the rib 40. Further, when substantially all of the body medial section 16 has been rolled about the body first end 14 and/or the rib 40, the roll 50 is generally planar having an upper side 52 and a lower side 54, as shown in FIGS. 4 and 5, respectively. When a condom 10 is put on, the user typically orients the roll 50 so that the lower side 54 is disposed at the tip of an erect penis and unrolls the condom 10 downwardly as indicated by arrow "B" in FIG. 2.

The condom 10 further includes an indicia 60, best shown in FIG. 5, disposed on the roll lower side 54. The indicia 60 provides a visual indication as to the orientation of the roll 50. That is, the indicia 60 is generally not visible when the roll 50 is viewed from a position generally normal to the roll upper side 52. Thus, a user simply orients the roll 50 so that the user cannot see the indicia 60 and then unrolls the condom 10 as described above. Preferably, the indicia 60 is fluorescent so that it may be easily seen, even in low light conditions. The indicia 60 may be printed, or otherwise applied, to the body inner side 26, or on the second end section inner side 28, adjacent to the body second end 18. Alternatively, the indicia 60 may be incorporated into the body 12. For example, a dye may be injected into the liquid latex used to form the condom 10. The indicia 60 is positioned so that, when the condom 10 is in the rolled configuration, the indicia 60 is disposed on the roll lower side 54. It is noted that, as shown in FIG. 1, the indicia 60 may be partially visible through the body 12. It is further noted that, when the condom 10 is in the rolled configuration, the indicia 60 is not clearly visible, or may not be visible at all, through the multiple layers that comprise the roll 50. Further, while the indicia 60 may have any shape or characteristics, in the preferred embodiment, the indicia 60 is a solid mark extending generally about the circumference of the lower side 54 of the roll 50.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

What is claimed is:

1. A condom comprising:
   a thin, elastic, generally tubular body having an open first end and an elongated medial section, said body having an inner side and an outer side;
   a closed second end section having an inner side and an outer side, said closed second end section coupled to said body, whereby said body and said closed second end section defining a generally enclosed space;
   said body structured to be reconfigured from a first rolled configuration, wherein said first end is rolled over said outer side of substantially all of said elongated medial section, to a second unrolled configuration, wherein said elongated medial section is substantially unrolled from said first end;
   wherein, when said body is in said first rolled configuration, said elongated medial section is rolled, generally snugly, about said first end thereby creating a roll, said roll having an upper side and a lower side; and
   an indicia disposed on said roll lower side.
2. The condom of claim 1 wherein:
   said roll is generally planar; and
   said indicia is generally not visible when said roll is viewed from a position generally normal to said roll upper side.
3. The condom of claim 1 wherein said indicia is fluorescent.
4. The condom of claim 1 wherein:
   said roll is a generally circular torus; and
   said indicia extends generally about the circumference of said lower side of said roll.
5. The condom of claim 4 wherein said indicia is fluorescent.
6. The condom of claim 4 wherein said indicia is a fluorescent section incorporated into said body.
7. A condom comprising:
   a thin, elastic tubular body having a first end, a medial section, a second end, an inner side and an outer side;
   a generally circular torus shaped rib, said rib coupled to said tubular body first end;
   a closed second end section having a thin, elastic generally dome shaped body with a peripheral edge, an inner side and an outer side, said peripheral edge coupled to said tubular body second end;
   said body structured to be reconfigured from a first rolled configuration, wherein said first end and said rib are rolled over said outer side of substantially all of said elongated medial section, to a second unrolled configuration, wherein said elongated medial section is substantially unrolled from said first end;
   wherein, when said body is in said first rolled configuration, said elongated medial section is rolled, generally snugly, about said rib thereby creating a roll, said roll having an upper side and a lower side; and
   an indicia disposed on said roll lower side.
8. The condom of claim 7 wherein:
   said roll is generally planar; and
   said indicia is generally not visible when said roll is viewed from a position generally normal to said roll upper side.
9. The condom of claim 7 wherein said indicia is fluorescent.
10. The condom of claim 7 wherein:
    said roll conforms to the generally circular torus of said rib; and
    said indicia extends generally about the circumference of said lower side of said roll.
11. The condom of claim 10 wherein said indicia is fluorescent.
12. The condom of claim 10 wherein said indicia is a fluorescent section incorporated into said body.
13. A rolled condom comprising:
    a roll being a generally circular torus having multiple layers of a medial section of a thin, elastic tubular body being wound about a first end of said body;
    said body further including a closed second end section;
    said roll having an upper side and a lower side; and
    an indicia disposed on said roll lower side.
14. The rolled condom of claim 13 wherein:
    said roll is generally planar; and
    said indicia is generally not visible when said roll is viewed from a position generally normal to said roll upper side.
15. The rolled condom of claim 13 wherein said indicia is fluorescent.
16. The rolled condom of claim 13 wherein:
    said roll is a generally circular torus; and
    said indicia extends generally about the circumference of said lower side of said roll.
17. The rolled condom of claim 16 wherein said indicia is fluorescent.
18. A rolled condom comprising:
    a roll being a generally circular torus having multiple layers of a medial section of a thin, elastic tubular body being wound about a rib coupled to a first end of said body;
    said body further including a closed second end section;
    said roll having an upper side and a lower side; and
    an indicia disposed on said roll lower side.
19. The rolled condom of claim 18 wherein:
    said roll is generally planar; and
    said indicia is generally not visible when said roll is viewed from a position generally normal to said roll upper side.
20. The rolled condom of claim 18 wherein said indicia is fluorescent.

* * * * *